United States Patent [19]

Sakai et al.

[11] 4,431,659

[45] Feb. 14, 1984

[54] 1-(ARYL)THIOCARBAMOYL-2-(ARYL)-3-PYRAZOLIDINONES AND THEIR NEMATICIDAL USE

[75] Inventors: Kunikazu Sakai; Minoru Suda; Kiyoshi Kondo, all of Kanagawa, Japan

[73] Assignee: FMC Corporation, Philadelphia, Pa.

[21] Appl. No.: 426,470

[22] Filed: Sep. 29, 1982

[51] Int. Cl.³ .................... A01N 47/38; C07D 231/06
[52] U.S. Cl. ................................. 424/273 P; 548/367
[58] Field of Search ................... 548/367; 424/273 P

[56] References Cited

U.S. PATENT DOCUMENTS 4,307,107  12/1981  Maurer et al. ..................... 548/367

*Primary Examiner*—Henry R. Jiles
*Assistant Examiner*—Bernard Dentz

*Attorney, Agent, or Firm*—Robert L. Andersen; H. Robinson Ertelt; Robert M. Kennedy

[57] ABSTRACT

Compounds of the general formula

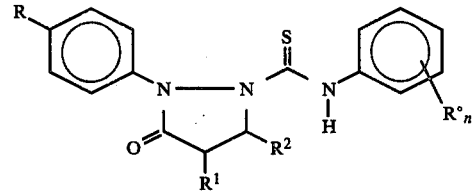

their method of preparation, and their use to control nematodes in agricultural crops are disclosed and exemplified.

7 Claims, No Drawings

1-(ARYL)THIOCARBAMOYL-2-(ARYL)-3-PYRAZOLIDINONES AND THEIR NEMATICIDAL USE

The present invention is directed to nematicidal compounds for control of nematodes which adversely affect agricultural crops. More particularly the invention is directed to novel nematicidal 1-(aryl)thiocarbamoyl-2-(aryl)-3-pyrazolidinones, formulations thereof, and to their use for treatment of nematodes.

The novel compounds of this invention are those having the general formula:

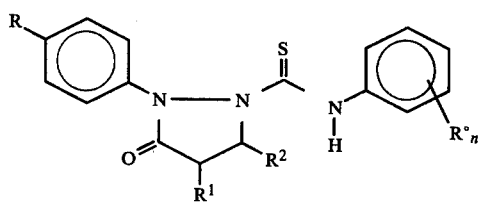

in which R is hydrogen, alkyl of 1 to 4 carbon atoms, or halogen; $R^1$ and $R^2$ are each hydrogen or alkyl of 1 to 4 carbon atoms; $R^o$ is hydrogen, halogen, alkyl of 1 to 4 carbon atoms, or alkoxy of 1 to 4 carbon atoms; n is 0, 1 or 2. When n is 2, each $R^o$ group may be the same or different.

In the foregoing and throughout the specification and claims the term halogen means chlorine, bromine, fluorine or iodine, preferably chlorine and bromine, and the term lower as applied to a hydrocarbyl group means such a group having 1 to 4 carbon atoms, straight or branched chain.

The compounds of this invention are further illustrated more specifically by reference to formula I-A as shown below:

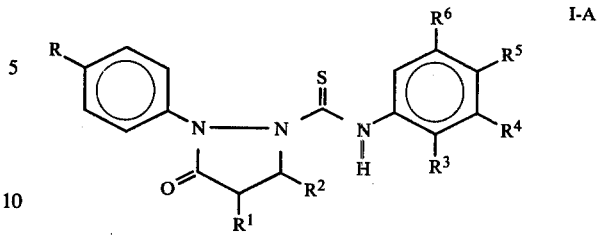

| Cmpd. No. | R | $R^1$ | $R^2$ | $R^3$ | $R^4$ | $R^5$ | $R^6$ |
|---|---|---|---|---|---|---|---|
| 1 | H | H | H | H | H | Cl | H |
| 2 | CH$_3$ | H | H | H | H | OC$_2$H$_5$ | H |
| 3 | CH$_3$ | H | H | Cl | H | H | H |
| 4 | CH$_3$ | H | H | H | Cl | H | H |
| 5 | CH$_3$ | H | H | H | H | Cl | H |
| 6 | CH$_3$ | H | H | Br | H | H | H |
| 7 | CH$_3$ | H | H | H | Br | H | H |
| 8 | CH$_3$ | H | H | H | H | Br | H |
| 9 | CH$_3$ | H | H | Cl | H | H | Cl |
| 10 | CH$_3$ | H | H | CH$_3$ | H | H | Cl |
| 11 | Cl | H | H | H | H | OC$_2$H$_5$ | H |
| 12 | Cl | H | H | Cl | H | H | H |
| 13 | Cl | H | H | H | Cl | H | H |
| 14 | Cl | H | H | H | H | Cl | H |
| 15 | Cl | H | H | Br | H | H | H |
| 16 | Cl | H | H | H | Br | H | H |
| 17 | Cl | H | H | H | H | Br | H |
| 18 | H | CH$_3$ | H | H | F | H | H |
| 19 | H | CH$_3$ | H | Cl | H | H | H |
| 20 | H | CH$_3$ | H | H | H | Cl | H |
| 21 | H | CH$_3$ | H | H | H | Br | H |
| 22 | H | CH$_3$ | H | I | H | H | H |
| 23 | H | CH$_3$ | H | Cl | H | H | Cl |
| 24 | H | CH$_3$ | H | CH$_3$ | H | Cl | H |
| 25 | H | CH$_3$ | H | CH$_3$ | H | H | Cl |
| 26 | H | H | CH$_3$ | H | H | H | H |
| 27 | H | H | CH$_3$ | H | H | Cl | H |

From the foregoing the compounds of this invention may be more specifically defined as compounds of formula I-A in which R is hydrogen, methyl or chloro
$R^1$ is hydrogen or methyl
$R^2$ is hydrogen or methyl
$R^3$ is hydrogen, halogen or methyl
$R^4$ is hydrogen or halogen
$R^5$ is hydrogen, halogen or lower alkoxy, and
$R^6$ is hydrogen or halogen Of particular interest are the compounds of formula I-A in which:

(a) $R^3$ is other than methyl if $R^1$ is methyl, R, $R^2$, $R^4$ and $R^6$ are each hydrogen, and $R^5$ is hydrogen or bromo;

(b) $R^3$ is other than bromo if $R^1$ is methyl, R, $R^2$, $R^4$ and $R^5$ are each hydrogen, and $R^6$ is hydrogen or bromo;

(c) $R^4$ and $R^6$ are not both chloro if $R^1$ is methyl and R, $R^2$, $R^3$, and $R^5$ are each hydrogen; or (d) $R^3$ and $R^5$ are not both chloro if $R^1$ is methyl and R, $R^2$, $R^4$ and $R^6$ are each hydrogen.

In the foregoing schedule of compounds there has been specifically exemplified the compounds defined above in which R, $R^1$ and $R^2$ are each hydrogen, compounds in which R is methyl or chloro when $R^1$ and $R^2$ are each hydrogen, compounds in which $R^1$ is methyl when R and $R^2$ are each hydrogen, and compounds in which $R^2$ is methyl when R and $R^1$ are each hydrogen.

The compounds of this invention are prepared by reacting a substituted 2-phenyl-3-pyrazolidinone (II) with a substituted phenyl isothiocyanate (III) in accordance with the following general reaction:

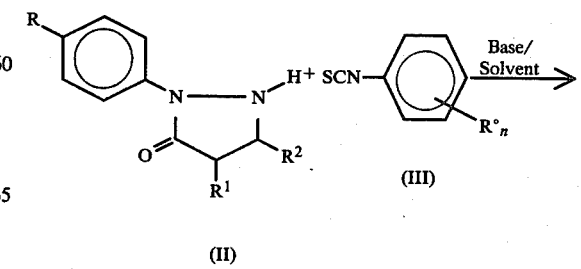

-continued

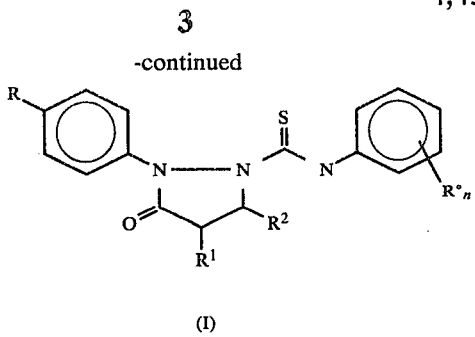

(I)

This reaction is suitably conducted in the presence of a base and a solvent. Suitable base/solvent systems include pyridine/toluene and sodium hydride/tetrahydrofuran. It will be apparent to those skilled in the art that other solvent/base systems may be selected without departing from the spirit of the invention.

Several methods for preparing the starting material (II) are known in the art. 2-Phenyl-3-pyrazolidinone may be prepared by the method of R. U. Rothenburg, Chem. Ber., 26, 2972–2975 (1893). 4-Methyl-2-phenyl-3-pyrazolidinone may be prepared by the method of K. Kemmner et al., Chem. Ber. 84, 10 (1951). 5-Methyl-2-phenyl-3-pyrazolidinone may be prepared by the method of L. Knorr et al., Chem. Ber., 25, 759–768 (1892). The remaining 2-(chloro or methyl substituted phenyl)-3-pyrazolidinones may be prepared by appropriate modifications of the method of H. Dorn et al., J. Prakt. Chem., 313, 1173 (1973). The foregoing literature references are hereby incorporated herein by reference.

The following examples illustrate preparation of the compounds described above.

EXAMPLE 1

Synthesis of 1-(4-chlorophenyl)thiocarbamoyl-2-phenyl-3-pyrazolidinone (Compound 1)

A mixture of 2.11 grams (0.013 mole) of 2-phenyl-3-pyrazolidinone, 2.21 grams (0.013 mole) of 4-chlorophenyl isothiocyanate and 0.5 ml of pyridine in 15 ml of toluene was heated at reflux for 9 hours. The reaction mixture was allowed to cool to room temperature forming a crystalline precipitate. The crystalline precipitate was collected by filtration to yield 3.92 grams of 1-(4-chlorophenylthiocarbamoyl)-2-phenyl-3-pyrazolidinone (mp 136°–139° C.).

Analysis calc'd for $C_{16}H_{14}ClN_3OS$: C 57.92; H 4.25; N 12.66; S 9.66; Cl 10.69; Found: C 58.01; H 4.22; N 12.79; S 9.70; Cl 10.76.

Compound numbers 18 through 27, characterized in Table I, were also synthesized in the manner of Example 1.

EXAMPLE 2

Synthesis of 1-(4-chlorophenyl)thiocarbamoyl-2-(4-chlorophenyl)-3-pyrazolidinone (Compound 14)

Under a dry argon atmosphere a solution of 1.6 grams (0.008 mole) of 2-(4-chlorophenyl)-3-pyrazolidinone in 13 ml of tetrahydrofuran was added dropwise to a stirred mixture of 0.4 gram (0.009 mole) of sodium hydride (55% oil suspension, oil removed by washing with hexane) in 8 ml of dry tetrahydrofuran while at room temperature. After complete addition, the reaction mixture was heated at 50° C. until gas evolution ceased, then cooled to room temperature. A solution of 1.4 grams (0.008 mole) of 4-chlorophenyl isothiocyanate in 8 ml of tetrahydrofuran was added to the reaction mixture and the resultant mixture stirred at room temperature for 14 hours. A saturated aqueous ammonium chloride solution was added to the reaction mixture and the total extracted with ethyl acetate. The organic extract was washed with a saturated aqueous sodium chloride solution, dried over anhydrous sodium sulfate and filtered. The solvent was removed by distillation under reduced pressure leaving a solid residue. The solid was purified by recrystallization from ethanol to afford 1.4 grams of 1-(4-chlorophenyl)thiocarbamoyl-2-(4-chlorophenyl)-3-pyrazolidinone (mp 121°–124° C.).

Analysis calc'd for $C_{16}H_{14}N_3OSCl_2$: C 52.47; H 3.58; N 11.47; S 8.75; Cl 19.36; Found: C 52.19; H 3.49; N 11.47; S 8.62; Cl 19.25.

Compounds 2 through 17, characterized in Table I, were prepared by the method of Example 2.

The starting material, 2-(4-chlorophenyl)-3-pyrazolidinone, used in Examples 1 and 2 may be prepared as shown in the following example.

EXAMPLE 3

Synthesis of 2-(4-chlorophenyl)-3-pyrazolidinone

To a stirred solution of 4.2 grams (0.05 mole) of sodium bicarbonate in 25 ml of water, 8.9 grams (0.05 mole) of (4-chlorophenyl)hydrazine hydrochloride was added portionwise. After complete addition the mixture was stirred until gas evolution ceased. To this mixture was added 5.5 grams (0.1 mole) of acrylonitrile and the total heated at 80° C. for 4.5 hours. The mixture was cooled and added to a solution of 9.8 grams of concentrated sulfuric acid in 29 ml of water at room temperature. The resultant mixture was heated for one hour at 40° C. and then at reflux for 2.5 hours. This mixture was cooled and added dropwise to a solution of 7.8 grams of sodium hydroxide in 11 ml of water, cooled by an ice bath and stirred for one hour after complete addition. A precipitate formed which was collected by filtration. The filter cake was washed with water, dried under reduced pressure and purified by recrystallization from ethanol to yield 2.78 grams of 2-(4-chlorophenyl)-3-pyrazolidinone (mp 120°–122° C.).

Analysis calc'd for $C_9H_9N_2OCl$: C 54.97; H 4.61; N 14.25; Cl 18.03; Found: C 54.65; H 4.63; N 14.08; Cl 17.93.

The nematicides of this invention, like most agricultural chemicals, are generally not applied full strength, but are formulated with agriculturally acceptable carriers normally employed for facilitating the dispersion of active ingredients, various additives, and optionally with other active ingredients, recognizing that the formulation and mode of application of a toxicant may affect the activity of the material. The present compounds may be applied, for example, as powders or liquids, the choice of application varying with the nematode species and environmental factors present at the particular locus of infestation. Thus, the compounds may be formulated as granules, as dusts, as wettable powders, as emulsifiable concentrates, as solutions, as dispersions, as controlled release compositions, and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of from about 0.5% up to about 99.5% by weight of the formulation. Substantially inactive ingredients such as adjuvants, diluents, and carriers may comprise from about 99.5% by weight to as low as about 0.5% by weight of the formulation. Surface active agents, if employed in the formulation, may be present at various concentrations, suitably in the range of 1 to 30% by weight. Provided below is a general description of exemplary types of formulations which may be employed for dispersion of the nematicides of the present invention.

Dusts are admixtures of the active ingredient with finely divided solid carriers and/or diluents such as talc, natural clays, kieselguhr, pyrophyllite, chalk, diatomaceous earths, calcium phosphates, calcium and magnesium carbonates, sulfur, lime, flours, and other organic and inorganic solid carriers. These finely divided formulations generally have an average particle size of less than about 50 microns (325 mesh, Standard U.S. Sieve Series). In most cases, the active ingredient will be present in dust formulations at a concentration in the range of 1 to 15%, and occasionally from 1% to about 30%, the balance of the composition typically comprising one or more agriculturally acceptable inerts as adjuvant, carrier, or diluent.

Wettable powders, also useful formulations for these nematicides, are in the form of finely divided particles which disperse readily in water or other liquid vehicles. The wettable powder is ultimately applied to the plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp <100° C.) are suitably formulated in the concentration range of 5 to 50% by weight, usually from 10 to 30%; high melting solids (mp >100° C.) being formulated in the range of 5 to 95% by weight, usually 50 to 85%. An agriculturally acceptable carrier or diluent, frequently including a small amount of a surfactant to facilitate wetting dispersion and suspension, accounts for the balance of the formulation.

Microencapsulated or other controlled release formulations may also be used with nematicides of this invention for control of nematodes.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the nematicide, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5% to 5% being surfactant and liquid carrier.

Flowables are similar to EC's except that the active ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in nematicidal formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the nematicidal composition.

Other useful formulations include simple solutions of the active ingredient in a relatively non-volatile solvent such as corn oil, kerosene, propylene glycol, or other organic solvents. This type of formulation is particularly useful for ultra low volume application.

The concentration of the nematicide in use dilution is normally in the range of about 2% to about 0.1%. Many variations of spraying, dusting, and controlled or slow release compositions in the art may be used by substituting or adding a compound of this invention into compositions known or apparent to the art.

Nematicidal compositions may be formulated and applied with other suitable active ingredients, including other nematicides, insecticides, acaricides, fungicides, plant regulators, herbicides, fertilizers, etc.

In applying the foregoing chemicals, an effective nematicidal amount must be applied. While the application rate will vary widely depending on the choice of compound, the formulation and mode of application, the plant species being protected and the planting density, a suitable use rate may be in the range of 0.5 to 25 kg/hectare, preferably 1 to about 20 kg/hectare. Trees and vines for example may require at least 5 kg/hectare whereas annuals such as corn may require considerably lower rates of application, for example 1 to 5 kg/hectare.

The compounds of this invention are usually applied by incorporating a formulation thereof into the soil in which agricultural crops are or are to be planted, i.e., the locus of infestation. Some of the compounds are active at the locus of infestation when applied to the above ground portions of the plant and may be so applied.

The following are specific examples of formulations which may be utilized in accordance with the present invention:

A typical 5% dust (wt/wt) formulation is as follows:

| | |
|---|---|
| Active ingredient (100% active basis) | 5% |
| Base | 95% |
| 96% Attaclay | |
| 2% highly purified sodium lignosulfonate (100%) | |
| 2% powdered sodium alkylnaphthalene sulfonate (75%) | |

A typical Attaclay granular formulation is as follows:

| | |
|---|---|
| Active ingredient | 5% |
| Attaclay | 95% |

A typical sand core granule formulation is as follows:

| FMC 75% base | | 6.64% |
|---|---|---|
| Active ingredient | 75% | |
| Sodium alkylnaphthalenesulfonate | 1% | |
| Sugar-free sodium based sulfonate of Kraft lignin | 4% | |
| Barden clay | 20% | |
| Polyvinyl acetate | | 0.75% |
| Water | | 1.00% |
| Silica (20/40 mesh) | | 91.61% |

The Attaclay granular formulation may be prepared by dissolving the active ingredient in a volatile solvent such as methylene chloride, then coating the attaclay with the resulting solution or by other methods well known to those skilled in the art, and allowing the solvent to evaporate. The sand core granule may be prepared by incorporating the active ingredient into a suitable base, then applying to sand to form a coated granule generally utilizing a sticker such as polyvinyl acetate.

The compounds of this invention were tested for biological activity as formulations of the active ingredient as an acetone solution, as a dust formulation, or as a granular formulation. The activity against root-knot nematode (*Meloidogyne incognita*) was determined by incorporating the compound of the invention in nematode infested soil at rates in the range of 25 ppm to 1.25 ppm. Several tomato plants were planted in the nematode infested soil. Two weeks after planting the tests were evaluated to ascertain the degree of galling on the roots of the plant, indicating the control provided by the test chemical.

The results, expressed as "knot index", are set forth in Table II. Knot index is a numerical designation assigned at evaluation, having the following meanings:

| Knot Index | Observed Degree of Control |
|---|---|
| 0 | No swellings - complete control |
| 1 | ~75% less swellings than control plants |
| 2 | ~50% less swellings than control plants |
| 3 | ~25% less swellings than control plants |
| 4 | About same as control plants - no control |

When the Knot Index is between 0 and 1 it is further subdivided as follows to indicate how close the degree of control is to 75% or 100%:

| Knot Index | Degree of Control |
|---|---|
| 0.8 | 80% |
| 0.5 | 90% |
| 0.1–0.4 | 95–99% |

The results reported in Table II are the average of the knot index assigned to each test. Where two or more different formulations, or batches thereof, were employed the average knot index for each is reported. The compounds of this invention were highly effective against root-knot nematodes.

The compounds of the invention were also tested by soil incorporation at rates in the range of 20 ppm to 5 ppm for control of stunt nematode (*Tylenchorynchus claytoni*) infestation of corn seedlings. Except for compound 12, which exhibited no control at 15 ppm, all compounds tested were effective in controlling stunt nematode. The percent control was in the range of 52.9% to 99.8%.

The compounds were similarly evaluated for control of lesion nematode (*Pratylenchus penetrans*) infestation of pea seedlings. Except for compound 9, which exhibited no control at 15 ppm, the compounds were highly effective in controlling lesion nematode. At 15 ppm the compounds exhibited a minimum of 27.6% control (compound 21) to a high of 92.6% (compound 20).

TABLE I 1-(ARYL)THIOCARBAMOYL-2-(ARYL)-3-PYRAZOLIDINONES

| Cmpd. No. | M.P. (°C.) | Empirical Formula | | C | H | N | S | Hal. |
|---|---|---|---|---|---|---|---|---|
| 1 | 136–139 | $C_{16}H_{14}ClN_3OS$ | Calcd | 57.92 | 4.25 | 12.66 | 9.66 | 10.69 |
| | | | Found | 58.01 | 4.22 | 12.79 | 9.70 | 10.76 |
| 2 | 118–120 | $C_{19}H_{21}N_3O_2S$ | Calcd | 64.20 | 5.95 | 11.82 | 9.02 | |
| | | | Found | 64.41 | 6.03 | 11.93 | 9.06 | |
| 3 | 103–104 | $C_{17}H_{16}N_3OSCl$ | Calcd | 59.04 | 4.66 | 12.15 | 9.27 | 10.25 |
| | | | Found | 58.92 | 4.64 | 12.22 | 9.46 | 10.20 |
| 4 | 134–136 | $C_{17}H_{16}N_3OSCl$ | Calcd | 59.04 | 4.66 | 12.15 | 9.27 | 10.25 |
| | | | Found | 59.04 | 4.71 | 12.23 | 9.15 | 9.83 |
| 5 | 134–138 | $C_{17}H_{16}N_3OSCl$ | Calcd | 59.04 | 4.66 | 12.15 | 9.27 | 10.25 |
| | | | Found | 58.83 | 4.67 | 12.13 | 9.35 | 10.17 |
| 6 | 122–124 | $C_{17}H_{16}N_3OSBr$ | Calcd | 52.32 | 4.13 | 10.77 | 8.22 | 20.47 |
| | | | Found | 52.27 | 4.13 | 10.82 | 8.32 | 20.19 |
| 7 | 135–137 | $C_{17}H_{16}N_3OSBr$ | Calcd | 52.32 | 4.13 | 10.77 | 8.22 | 20.47 |
| | | | Found | 52.50 | 4.17 | 11.31 | 8.13 | 19.51 |
| 8 | 135–137 | $C_{17}H_{16}N_3OSBr$ | Calcd | 52.32 | 4.13 | 10.77 | 8.22 | 20.47 |
| | | | Found | 52.11 | 4.18 | 10.78 | 8.24 | 19.93 |
| 9 | 109.5–110.5 | $C_{17}H_{15}N_3OSCl_2$ | Calcd | 53.69 | 3.98 | 11.05 | 8.43 | 18.64 |
| | | | Found | 53.33 | 4.31 | 10.74 | 8.27 | 18.01 |
| 10 | 119–121 | $C_{18}H_{18}N_3OSCl$ | Calcd | 60.08 | 5.04 | 11.68 | 8.91 | 9.85 |
| | | | Found | 60.07 | 5.20 | 11.71 | 9.07 | 9.45 |
| 11 | 121–123 | $C_{18}H_{18}N_3O_2SCl$ | Calcd | 56.72 | 4.83 | 11.18 | 8.53 | 9.45 |
| | | | Found | 57.54 | 4.92 | 11.24 | 8.36 | 9.23 |
| 12 | 112–113 | $C_{16}H_{13}N_3OSCl_2$ | Calcd | 52.47 | 3.58 | 11.47 | 8.75 | 19.36 |
| | | | Found | 52.58 | 3.52 | 11.49 | 8.69 | 19.23 |
| 13 | 140–141 | $C_{16}H_{13}N_3OSCl_2$ | Calcd | 52.47 | 3.58 | 11.47 | 8.75 | 19.36 |
| | | | Found | 52.45 | 3.58 | 11.48 | 8.67 | 19.11 |
| 14 | 121–124 | $C_{16}H_{13}N_3OSCl_2$ | Calcd | 52.47 | 3.58 | 11.47 | 8.75 | 19.36 |
| | | | Found | 52.19 | 3.49 | 11.47 | 8.62 | 19.25 |

TABLE I-continued

1-(ARYL)THIOCARBAMOYL-2-(ARYL)-3-PYRAZOLIDINONES

| Cmpd. No. | M.P. (°C.) | Empirical Formula | | C | H | N | S | Hal. |
|---|---|---|---|---|---|---|---|---|
| 15 | 104–106 | $C_{16}H_{13}N_3OSBrCl$ | Calcd | 46.79 | 3.19 | 10.23 | 7.81 | |
| | | | Found | 46.65 | 3.17 | 10.34 | 7.91 | |
| 16 | 143–145 | $C_{16}H_{13}N_3OSBrCl$ | Calcd | 46.79 | 3.19 | 10.23 | 7.81 | |
| | | | Found | 46.68 | 3.18 | 10.26 | 7.55 | |
| 17 | 132–134 | $C_{16}H_{13}N_3OSBrCl$ | Calcd | 46.79 | 3.19 | 10.23 | 7.81 | |
| | | | Found | 46.84 | 3.32 | 10.27 | 7.78 | |
| 18 | 128–130 | $C_{17}H_{16}N_3OSF$ | Calcd | 61.99 | 4.90 | 12.76 | 9.73 | 5.77 |
| | | | Found | 62.25 | 4.97 | 12.80 | — | — |
| 19 | 125–126 | $C_{17}H_{16}N_3OSCl$ | Calcd | 59.04 | 4.66 | 12.15 | 9.27 | 10.25 |
| | | | Found | 58.99 | 4.66 | 12.15 | 9.42 | 10.03 |
| 20 | 131–133 | $C_{17}H_{16}N_3OSCl$ | | | | | | |
| 21 | 142.5–144 | $C_{17}H_{16}N_3OSBr$ | Calcd | 52.32 | 4.13 | 10.77 | 8.22 | 20.47 |
| | | | Found | 52.40 | 4.10 | 10.79 | 8.46 | 20.00 |
| 22 | 111–112 | $C_{17}H_{16}N_3OSI$ | Calcd | 46.69 | 3.63 | 9.61 | 7.33 | 29.02 |
| | | | Found | 47.05 | 3.68 | 9.63 | 7.53 | — |
| 23 | 135–136 | $C_{17}H_{15}N_3OSCl_2$ | Calcd | 53.69 | 3.98 | 11.05 | 8.43 | 18.64 |
| | | | Found | 53.86 | 3.98 | 11.09 | 8.67 | 18.66 |
| 24 | 121–123 | $C_{18}H_{18}N_3OSCl$ | Calcd | 60.08 | 5.04 | 11.68 | 8.91 | 9.85 |
| | | | Found | 60.09 | 5.06 | 11.81 | 9.14 | 9.71 |
| 25 | 114–116 | $C_{18}H_{18}N_3OSCl$ | Calcd | 60.08 | 5.04 | 11.68 | 8.91 | 9.85 |
| | | | Found | 60.68 | 5.11 | 11.71 | 8.45 | 9.46 |
| 26 | 153–155 | $C_{17}H_{17}N_3OS$ | | | | | | |
| 27 | 156–161 | $C_{17}H_{16}ClN_3OS$ | Calcd | 59.04 | 4.66 | 12.15 | 9.27 | 10.25 |
| | | | Found | 59.29 | 4.66 | 12.33 | 9.14 | 10.20 |

TABLE II

| Cmpd. No. | Formulation Type | Application Rate (ppm) | Knot Index Formulation of Test # 1 | 2 | 3 | 4 |
|---|---|---|---|---|---|---|
| 1 | 5% Dust | 25 | 0.0 | 0.0 | 0.0 | |
| | | 10 | — | 2.0 | 1.0 | |
| | | 5 | — | — | 4.0 | |
| 2 | 5% Dust | 25 | 0.0 | 0.0 | — | |
| | | 10 | — | 0.65 | 3.5 | |
| | | 5 | — | — | 4.0 | |
| 3 | 5% Dust | 25 | 0.0 | 0.0 | — | |
| | | 10 | — | 0.65 | 0.12 | |
| | | 5 | — | — | 1.25 | |
| | | 2.5 | — | — | 3.75 | |
| 4 | 5% Dust | 25 | 0.0 | 0.0 | — | |
| | | 10 | — | 0.25 | 0.0 | |
| | | 5 | — | — | 0.8 | |
| | | 2.5 | — | — | 4.0 | |
| 5 | 5% Dust | 25 | 0.0 | 0.0 | — | |
| | | 10 | — | 0.4 | 0.5 | |
| | | 5 | — | — | 1.25 | |
| | | 2.5 | — | — | 3.25 | |
| 6 | 5% Dust | 25 | 0.25 | 0.0 | — | — |
| | | 10 | — | 0.65 | 0.0 | — |
| | | 5 | — | — | 0.0 | 2.5 |
| | | 2.5 | — | — | 0.0 | 4.0 |
| 7 | 5% Dust | 25 | 0.40 | 0.0 | — | |
| | | 10 | — | 0.73 | 1.0 | |
| | | 5 | — | — | 1.0 | |
| | | 2.5 | — | — | 4.0 | |
| 8 | 5% Dust | 25 | 0.0 | 0.0 | — | |
| | | 10 | — | 0.0 | 0.62 | |
| | | 5 | — | — | 2.0 | |
| | | 2.5 | — | — | 3.8 | |
| 9 | 5% Dust | 25 | 0.0 | 0.0 | — | |
| | | 10 | — | 0.0 | 4.0 | |
| 10 | 5% Dust | 25 | 0.25 | 0.0 | — | |
| | | 10 | — | 0.5 | 0.25 | |
| | | 5 | — | — | 3.0 | |
| | | 2.5 | — | — | 4.0 | |
| 11 | 5% Dust | 25 | 0.0 | 0.25 | — | |
| | | 10 | — | 0.95 | 0.5 | |
| | | 5 | — | — | 1.5 | |
| | | 2.5 | — | — | 4.0 | |
| 12 | 5% Dust | 25 | 0.0 | 0.0 | — | |
| | | 10 | — | 0.0 | 0.37 | |
| | | 5 | — | — | 1.25 | |
| | | 2.5 | — | — | 4.0 | |
| 13 | 5% Dust | 25 | 0.0 | 2.0 | — | |
| | | 10 | — | 3.0 | 0.75 | |
| | | 5 | — | — | 4.0 | |
| 14 | 5% Dust | 25 | 0.4 | 0.0 | — | |
| | | 10 | — | 0.25 | 0.37 | |
| | | 5 | — | — | 0.9 | |
| | | 2.5 | — | — | 4.0 | |
| 15 | 5% Dust | 25 | 0.0 | 0.0 | — | |
| | | 10 | — | 0.0 | 3.0 | |
| | | 5 | — | — | 3.0 | |
| | | 2.5 | — | — | 4.0 | |
| 16 | 5% Dust | 25 | 2.0 | 1.5 | — | |
| | | 10 | — | 3.5 | — | |
| 17 | 5% Dust | 25 | 0.25 | 0.0 | — | |
| | | 10 | — | 0.5 | 0.62 | |
| | | 5 | — | — | 1.50 | |
| | | 2.5 | — | — | 4.0 | |
| 18 | 5% Dust | 25 | 2.0 | 1.0 | — | |
| | | 10 | — | 1.75 | — | |
| 19 | 5% Dust | 25 | 0.5 | 0.13 | — | |
| | | 10 | — | 0.78 | 1.20 | |
| | | 5 | — | — | 4.0 | |
| 20 | 5% Dust | 25 | 0.0 | 0.05 | 0.0 | — |
| | | 10 | — | 0.5 | 0.75 | 0.85 |
| | | 5 | — | — | 0.83 | 2.75 |
| | | 2.5 | — | — | — | 4.0 |
| | 5% Sand Granule | 25 | — | 4.0 | | |
| | 5% Attaclay Granule | 25 | — | 1.5 | | |
| | | 10 | — | 3.0 | | |
| | | 5 | — | 4.0 | | |
| 21 | 5% Dust | 25 | 2.0 | 0.2 | — | — |
| | | 10 | — | 0.6 | 2.0 | 0.87 |
| | | 5 | — | — | 2.75 | 3.25 |
| | | 2.5 | — | — | 3.0 | 4.0 |
| 22 | 5% Dust | 25 | 1.0 | 0.75 | | |
| | | 10 | — | 3.0 | | |
| 23 | 5% Dust | 25 | 0.9 | 0.0 | — | |
| | | 10 | — | 0.58 | 0.95 | |
| | | 5 | — | — | 2.25 | |
| | | 2.5 | — | — | 1.75 | |
| 24 | 5% Dust | 25 | 1.50 | 0.9 | | |
| | | 10 | — | 2.0 | | |
| 25 | 5% Dust | 25 | 0.35 | 0.0 | — | — |
| | | 10 | — | 0.2 | 1.25 | — |
| | | 5 | — | — | 1.75 | 0.95 |
| | | 2.5 | — | — | 3.75 | 3.25 |
| | | 1.25 | — | — | — | 4.0 |
| 26 | 5% Dust | 25 | 2.0 | 0.78 | | |

TABLE II-continued

| Cmpd. No. | Formulation Type | Application Rate (ppm) | Knot Index Formulation of Test # | | | |
|---|---|---|---|---|---|---|
| | | | 1 | 2 | 3 | 4 |
| | | 10 | — | 2.25 | | |
| 27 | 5% Dust | 25 | 0.0 | 0.0 | 0.95 | |
| | | 10 | — | 1.0 | 4.0 | |

We claim:

1. A compound of the formula

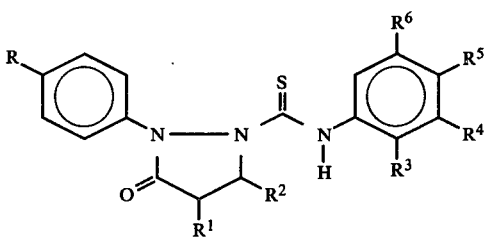

in which

R is hydrogen, methyl or chloro
$R^1$ is hydrogen or methyl
$R^2$ is hydrogen or methyl
$R^3$ is hydrogen, halogen or methyl
$R^4$ is hydrogen or halogen
$R^5$ is hydrogen, halogen, or lower alkoxy
$R^6$ is hydrogen, or halogen with the provisos:

(a) $R^3$ is other than methyl when $R^1$ is methyl, R, $R^2$, $R^4$ and $R^6$ are each hydrogen and $R^5$ is hydrogen or bromo;

(b) $R^3$ is other than bromo when $R^1$ is methyl, R, $R^2$, $R^4$ and $R^5$ are each hydrogen, and $R^6$ is hydrogen or bromo;

(c) $R^4$ and $R^6$ are not both chloro when $R^1$ is methyl and R, $R^2$, $R^3$, and $R^5$ are each hydrogen;

(d) $R^3$ and $R^5$ are not both chloro if $R^1$ is methyl and R, $R^2$, $R^4$ and $R^6$ are each hydrogen.

2. The compound of claim 1 in which R, $R^1$ and $R^2$ are each hydrogen.

3. A compound of claim 1 in which R is methyl or chloro and $R^1$ and $R^2$ are each hydrogen.

4. A compound of claim 1 in which $R^2$ is methyl and R and $R^1$ are each hydrogen.

5. A compound selected from the group consisting of:
(1) 1-(4-chlorophenyl)thiocarbamoyl-2-phenyl-3-pyrazolidinone
(2) 1-(4-ethoxyphenyl)thiocarbamoyl-2-(4-methylphenyl)-3-pyrazolidinone
(3) 1-(2-chlorophenyl)thiocarbamoyl-2-(4-methylphenyl)-3-pyrazolidinone
(4) 1-(3-chlorophenyl)thiocarbamoyl-2-(4-methylphenyl)-3-pyrazolidinone
(5) 1-(4-chlorophenyl)thiocarbamoyl-2-(4-methylphenyl)-3-pyrazolidinone
(6) 1-(2-bromophenyl)thiocarbamoyl-2-(4-methylphenyl)-3-pyrazolidinone
(7) 1-(3-bromophenyl)thiocarbamoyl-2-(4-methylphenyl)-3-pyrazolidinone
(8) 1-(4-bromophenyl)thiocarbamoyl-2-(4-methylphenyl)-3-pyrazolidinone
(9) 1-(2,5-dichlorophenyl)thiocarbamoyl-2-(4-methylphenyl)-3-pyrazolidinone
(10) 1-(5-chloro-2-methylphenyl)thiocarbamoyl-2-(4-methylphenyl)-3-pyrazolidinone
(11) 1-(4-ethoxyphenyl)thiocarbamoyl-2-(4-chlorophenyl)-3-pyrazolidinone
(12) 1-(2-chlorophenyl)thiocarbamoyl-2-(4-chlorophenyl)-3-pyrazolidinone
(13) 1-(3-chlorophenyl)thiocarbamoyl-2-(4-chlorophenyl)-3-pyrazolidinone
(14) 1-(4-chlorophenyl)thiocarbamoyl-2-(4-chlorophenyl)-3-pyrazolidinone
(15) 1-(2-bromophenyl)thiocarbamoyl-2-(4-chlorophenyl-3-pyrazolidinone
(16) 1-(3-bromophenyl)thiocarbamoyl-2-(4-chlorophenyl)-3-pyrazolidinone
(17) 1-(4-bromophenyl)thiocarbamoyl-2-(4-chlorophenyl)-3-pyrazolidinone
(18) 1-(3-fluorophenyl)thiocarbamoyl-4-methyl-2-phenyl-3-pyrazolidinone
(19) 1-(2-chlorophenyl)thiocarbamoyl-4-methyl-2-phenyl-3-pyrazolidinone
(20) 1-(4-chlorophenyl)thiocarbamoyl-4-methyl-2-phenyl-3-pyrazolidinone
(21) 1-(4-bromophenyl)thiocarbamoyl-4-methyl-2-phenyl-3-pyrazolidinone
(22) 1-(2-iodophenyl)thiocarbamoyl-4-methyl-2-phenyl-3-pyrazolidinone
(23) 1-(2,5-dichlorophenyl)thiocarbamoyl-4-methyl-2-phenyl-3-pyrazolidinone
(24) 1-(4-chloro-2-methylphenyl)thiocarbamoyl-4-methyl-2-phenyl-3-pyrazolidinone
(25) 1-(5-chloro-2-methylphenyl)thiocarbamoyl-4-methyl-2-phenyl-3-pyrazolidinone
(26) 1-(phenyl)thiocarbamoyl-5-methyl-2-phenyl-3-pyrazolidinone
(27) 1-(4-chlorophenyl)thiocarbamoyl-5-methyl-2-phenyl-3-pyrazolidinone.

6. A nematicidal composition comprising a nematicidally effective amount of a compound of claim 1, 2, 3, 4 or 5 in admixture with at least one agriculturally acceptable adjuvant, diluent, or carrier.

7. A method for controlling nematodes in agricultural crops comprising applying to the locus of infestation a nematicidal amount of a compound of claim 1, 2, 3, 4 or 5.

* * * * *